United States Patent [19]

Berg

[11] Patent Number: 4,931,145

[45] Date of Patent: Jun. 5, 1990

[54] SEPARATION OF BENZENE FROM ACETONE BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 421,825

[22] Filed: Oct. 16, 1989

[51] Int. Cl.$^5$ .................... B01D 3/36; C07C 7/06; C07C 45/84
[52] U.S. Cl. .................... 203/69; 203/44; 568/411; 585/807; 585/867
[58] Field of Search .................... 203/69, 44; 568/411, 568/410; 585/800, 804, 867

[56] References Cited

U.S. PATENT DOCUMENTS

| | | | |
|---|---|---|---|
| 2,212,810 | 8/1940 | Field | 568/411 |
| 3,419,477 | 12/1968 | Mattia | 568/411 |
| 3,689,375 | 9/1972 | Furukawa et al. | 568/411 |
| 4,113,575 | 9/1978 | Dale | 568/411 |

FOREIGN PATENT DOCUMENTS 1142354 1/1963 Fed. Rep. of Germany ...... 568/411

*Primary Examiner*—Wilbur Bascomb

[57] ABSTRACT

Acetone cannot be easily separated from benzene in high purity by distillation because of the closeness of their vapor pressures. Acetone can be readily removed from benzene by azeotropic distillation using certain aromatic hydrocarbons. Typical effective azeotropic distillation agents are: toluene, ethyl benzene and mesitylene.

10 Claims, No Drawings

SEPARATION OF BENZENE FROM ACETONE BY AZEOTROPIC DISTILLATION

FIELD OF THE INVENTION

This invention relates to a method for separating benzene from acetone using certain aromatic hydrocarbons as the agent in azeotropic distillation.

DESCRIPTION OF PRIOR ART

Azeotropic distillation is the method of separating close boiling compounds from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require wither fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The separation of benzene, B.P.=80.1° C. from acetone, B.P.=56.2° C. would appear to be readily accomplished by rectification since an azeotrope is not formed. The boiling point difference of 23.9° C. appears to be ample and the overall relative volatility is about 2, see Example 1 below. In practice, it is found however that getting the last traces of benzene out of acetone is difficult to do by rectification. The poisonous properties of benzene make it imperative that none be left in acetone if it is to be marketable. Table 1 lists the boiling point of several acetone-benzene mixtrues and shows that the boiling point change is very slight at high acetone concentrations. While the overall relative volatility of acetone to benzene is 2, the relative volatility at high concentrations approaches 1.

TABLE 1

| Boiling Point of Several Acetone - Benzene mixtures | | | |
|---|---|---|---|
| Percent Acetone | Percent Benzene | B.P. °C. | B.P., °F. |
| 100 | 0 | 50.4 | 122.7 |
| 97 | 3 | 50.6 | 123.0 |
| 94 | 6 | 50.8 | 123.4 |
| 92 | 8 | 50.9 | 123.6 |
| 87 | 13 | 51.1 | 124.0 |
| 80 | 20 | 51.9 | 125.4 |
| 69 | 31 | 53.1 | 127.6 |

Azeoptropic distillation would be an attractive method of effecting the separation of benzene from acetone if agents can be found that (1) will increase the relative volatility of acetone to benzene at high acetone concentrations and (2) are easy to recover from acetone. Azeotropic distillation typically requires the addition of about as much agent as acetone to be boiled up in the column which increases the heat requirement as well as somewhat larger diameter plates to accomodate the increase of liquid and vapor in the column. In addition, a method of recovery of the azeotrope forming agent from the acetone must be provided. The easiest method is when the azeotrope forming agent is immiscible with water which allows the acetone to be easily extracted by water washing.

OBJECTIVE OF THE INVENTION

The objective of this invention is to provide a process or method of azeotropic distillation that will enhance the relative volatility of acetone to benzene in their separation in a rectification column. It is a further object of this invention to identify organic compounds which in addition to the above constraints, are stable, can be separated from acetone by solvent extraction and can be recycled to the azeotropic distillation and reused with little decomposition.

SUMMARY OF THE INVENTION

The objects of this invention are provided by a process for separating benzene from acetone which entails the use of certain aromatic hydrocarbons in an azeotropic distillation process.

DETAILED DESCRIPTION OF THE INVENTION

I have discovered that certain aromatic hydrocarbons will effectively enhance the relative volatility of acetone to benzene and permit the separation of acetone from benzene by rectification when employed as the agent in azeotropic distillation. Table 2 lists the compounds that I have found to be effective.

TABLE 2

| Effective Azeotrope Forming Agents | | | |
|---|---|---|---|
| Agent | Rel. Vol. | Agent | Rel. Vol. |
| Toluene | 1.2 | Cumene | 1.9 |
| Ethyl benzene | 2.0 | Mesitylene | 2.0 |
| o-Xylene | 1.4 | o-Diethyl benzene | 1.8 |
| m-Xylene | 1.5 | p-Diisopropyl benzene | 2.3 |
| p-Xylene | 1.1 | | |

The compounds which are effective are toluene, ethyl benzene, o-xylene, m-xylene, p-xylene, cumene (isopropyl benzene), mesitylene, o-diethyl benzene and p-diisopropyl benzene.

The data in Table 2 was obtained in a vapor-liquid equilibrium still. In each case the starting material was a mixture containing 50% azeotrope former and about 90% acetone-10% benzene mixture. The data in Table 2 indicates, for example, that one part of ethyl benzene mixed with one part of the acetone-benzene mixture gives a relative volatility of 2.0. Table 3 lists the data obtained in a multiplate rectification column.

TABLE 3

| Data From Runs Made In Rectification Column | | | | | |
|---|---|---|---|---|---|
| Agent | Column | Time, hrs. | Weight % Acetone | Weight % Benzene | Relative Volatility |
| Toluene | Overhead | 0 | 54.4 | 46.6 | |
| " | Bottoms | | 10.7 | 89.3 | |
| " | Overhead | 0.5 | 88.7 | 11.3 | 1.21 |
| " | Bottoms | | 27 | 73 | |
| " | Overhead | 1 | 93.4 | 6.6 | 1.20 |
| " | Bottoms | | 41.3 | 58.7 | |
| " | Overhead | 1.5 | 88.9 | 11.1 | 1.198 |
| " | Bottoms | | 29 | 71 | |
| Toluene | Overhead | 0 | 98.4 | 1.6 | |
| " | Bottoms | | 64.7 | 35.3 | |
| " | Overhead | 0.5 | 99.2 | 0.8 | |

TABLE 3-continued

| | Data From Runs Made In Rectification Column | | | | |
|---|---|---|---|---|---|
| Agent | Column | Time, hrs. | Weight % Acetone | Weight % Benzene | Relative Volatility |
| | Bottoms | | 66.9 | 33.1 | |
| " | Over-head | 1 | 99.9 | 0.1 | |
| | Bottoms | | 68.1 | 31.9 | |
| " | Over-head | 1.5 | 99.9 | 0.1 | |
| | Bottoms | | 75.8 | 24.2 | |

THE USEFULNESS OF THE INVENTION

The usefulness or utility of this invention can be demonstrated by referring to the data in Tables 2 and 3. All the successful azeotrope forming agents show that acetone can be separated rom benzene by means of distillation in a rectification column and that the ease of separation as measured by relative volatility is considerable. Without these azeotrope forming agents, only a slight improvement will occur in a rectification column.

WORKING EXAMPLES

Example 1

Eighty grams of acetone and 20 grams of benzene were charged to an Othmer type vapor-liquid equilibrium still and refluxed for two hours. Analysis by gas chromatography gave a vapor composition of 88.9% acetone, 11.1% benzene; a liquid composition of 80% acetone, 20% benzene. This indicates a relative volatility of 2.0.

Example 2

Eighty grams of acetone, 20 grams of benzene and 80 grams of ethyl benzene were charged to the vapor-liquid equilibrium still and refluxed for two hours. Analysis gave a vapor composition of 96.1% acetone, 3.9% benzene, a liquid composition of 92.6% acetone, 7.4% benzene which is a relative volatility of 2.0.

Example 3

A four foot long perforated plate rectification column was calibrated with m-xylene and o-xylene which possesses a relative volatility of 1.1 and found to have 16.5 theoretical plates. A solution comprising 300 grams of benzene, 50 grams of acetone and 100 grams of toluene was placed in the stillpot and heated. After a half hour of refluxing at total reflux, anlaysis was made by gas chromatography. The over head composition as 88.7% acetone, 11.3% benzene and the stillpot analysis was 27% acetone, 73% benzene. Using these compositions in the Fenske equation with the number of theoretical plates in the column being 16.5, gave an average relative volatility of 1.21 for each theoretical plate. The run was continued with sampling after one hour and 1.5 hours. The data is reported in Table 3.

Example 4

In the same column used in Example 3 was placed 100 grams of benzene, 300 grams of acetone and 100 grams of toluene. After one hour of refluxing at total reflux, the overhead analysis was 99.9% acetone, 0.1% benzene and the stillpot analysis was 68.1% acetone, 31.9% benzene. This is a relative volatility too high to measure accurately and shows that very high purity acetone can be obtained with toluene as the azeotrope forming agent. These data are listed in Table 3.

I claim:

1. A method for recovering acetone from a mixture of acetone and benzene which comprises distilling a mixture of acetone and benzene in a rectification column in the presence of an azeotrope forming agent, recovering the acetone and the azeotrope forming compound as overhead product, obtaining the benzene from the stillpot, wherein said azeotrope forming agent is an aromatic hydrocarbon containing seven to twelve carbon atoms.

2. The method of claim 1 in which the azeotrope forming agent is toluene.

3. The method of claim 1 in which the azeotrope forming agent is ethyl benzene.

4. The method of claim 1 in which the azeotrope forming agent is o-xylene.

5. The method of claim 1 in which the azeotrope forming agent is m-xylene.

6. The method of claim 1 in which the azeotrope forming agent is p-xylene.

7. The method of claim 1 in which the azeotrope forming agent is cumene (isopropyl benzene).

8. The method of claim 1 in which the azeotrope forming agent is mesitylene.

9. The method of claim 1 in which the azeotrope forming agent is o-diethyl benzene.

10. The method of claim 1 in which the azeotrope forming agent is p-diisopropyl benzene.

* * * * *